United States Patent
Kurihara (10) Patent No.: US 9,655,790 B2
(45) Date of Patent: May 23, 2017

(54) ABSORBENT ARTICLE AND MANUFACTURING METHOD THEREFOR

(71) Applicant: DAIO PAPER CORPORATION, Shikokuchuo-shi, Ehime (JP)

(72) Inventor: Ryoko Kurihara, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 19 days.

(21) Appl. No.: 14/403,440

(22) PCT Filed: May 28, 2013

(86) PCT No.: PCT/JP2013/064750
§ 371 (c)(1),
(2) Date: Nov. 24, 2014

(87) PCT Pub. No.: WO2013/180118
PCT Pub. Date: Dec. 5, 2013

(65) Prior Publication Data
US 2015/0119843 A1    Apr. 30, 2015

(30) Foreign Application Priority Data
May 28, 2012 (JP) ................................ 2012-120710

(51) Int. Cl.
*A61F 13/15* (2006.01)
*A61F 13/511* (2006.01)
(Continued)

(52) U.S. Cl.
CPC .. *A61F 13/51108* (2013.01); *A61F 13/15203* (2013.01); *A61F 13/15699* (2013.01);
(Continued)

(58) Field of Classification Search
CPC .......... A61F 13/51104; A61F 13/51108; A61F 13/5116; A61F 13/5125; A61F 2013/51078; A61F 2013/51083; A61F 2013/51178
See application file for complete search history.

(56) References Cited

U.S. PATENT DOCUMENTS 4,781,710 A * 11/1988 Megison ............... A61F 13/47
604/378
6,610,173 B1 * 8/2003 Lindsay ............... D21F 11/006
162/109
(Continued)

FOREIGN PATENT DOCUMENTS

JP    2002-165830    6/2002
JP    2004-174234    6/2004
(Continued)

*Primary Examiner* — Bradley Philips
(74) *Attorney, Agent, or Firm* — Norris McLaughlin & Marcus, P.A.

(57) ABSTRACT

An absorbent article has an absorber disposed between a permeable front surface sheet and a rear surface sheet of a non-woven fabric; wherein the front surface sheet is provided with ridged convex portions continuing in the longitudinal direction of the absorbent article at a specified interval in the width direction of the absorbent article, and provided with dot-like concave embossments at the right side adjacent position and the left side adjacent position alternately at an interval in the longitudinal direction of the absorbent article on the both sides of each of the convex portions, and the concave embossments are arranged in a zigzag pattern as a whole. The convex portion is an inclined surface having a relatively steep gradient on one side and a relatively gentle gradient on the other side, and the cross-sectional shape of the convex portion is an asymmetrical shape.

4 Claims, 7 Drawing Sheets

(51) Int. Cl.
*A61F 13/472* (2006.01)
*A61F 13/512* (2006.01)
*A61F 13/51* (2006.01)

(52) U.S. Cl.
CPC .. *A61F 13/15707* (2013.01); *A61F 13/15731* (2013.01); *A61F 13/15747* (2013.01); *A61F 13/15804* (2013.01); *A61F 13/472* (2013.01); *A61F 13/5116* (2013.01); *A61F 13/5125* (2013.01); *A61F 13/51104* (2013.01); *A61F 2013/15365* (2013.01); *A61F 2013/51078* (2013.01); *A61F 2013/51083* (2013.01)

(56) References Cited

U.S. PATENT DOCUMENTS

| | | |
|---|---|---|
| 2010/0069867 A1 | 3/2010 | Noda et al. |
| 2010/0178456 A1 | 7/2010 | Kuroda et al. |
| 2010/0249740 A1 * | 9/2010 | Miyamoto ........ A61F 13/51104 604/384 |
| 2012/0226250 A1 | 9/2012 | Sato et al. |
| 2013/0178815 A1 * | 7/2013 | Ohashi .................... A61F 13/49 604/380 |

FOREIGN PATENT DOCUMENTS

| | | | |
|---|---|---|---|
| JP | 2007-151678 A | 6/2007 | |
| JP | 2008/072631 | 6/2008 | |
| JP | 2008/146541 | 12/2008 | |
| JP | 2009-291473 | 12/2009 | |
| JP | 2011-131044 | 7/2011 | |
| JP | WO 2012043843 A1 * | 4/2012 | ............. A61F 13/49 |

* cited by examiner

RELATED ART

Fig. 12

RELATED ART

ABSORBENT ARTICLE AND MANUFACTURING METHOD THEREFOR

BACKGROUND OF THE INVENTION

This invention relates to an absorbent article such as sanitary napkins, incontinence liners, incontinence pads, discharge sheets, or the like to reduce dampness and prevent a body fluid from leaking down provided with a front surface sheet soft to skin having a decreased area in contact with the skin and a manufacturing method therefor.

Conventionally, front surface sheets of absorbent articles provided in the market are provided with appropriate emboss patterns depending on various purposes such as eliminating skin troubles by means of decreasing an area in contact with skin, providing texture, increasing a spot absorbency, or the like. One of this kind includes the prior art described below, for example.

Figure 11:
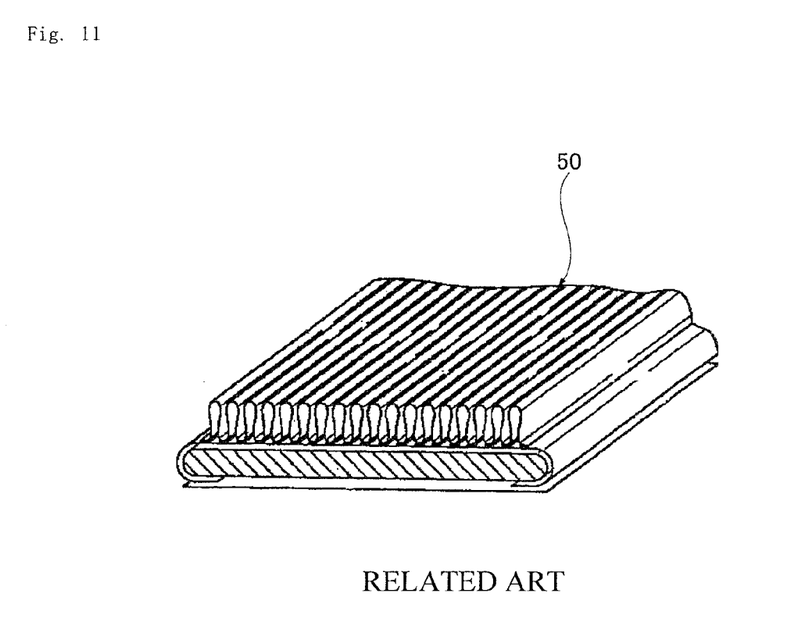
FIG. 11 is a cutaway perspective view of Example 1 of a conventional front surface sheet.

Firstly, as illustrated in FIG. 11, Japanese Unexamined Patent Application Publication No. 2002-165830 proposes a front surface sheet 50 for an absorbent article in which concave and convex shapes are formed in a skin abutment side when worn. When the absorbent article using the front surface sheet 50 is worn, the concave and convex shapes are transformed flexibly following a body shape and movement, and the concave portion of the concave and convex shapes captures high-viscosity excreta so as to separate said high-viscosity excreta and the body.

Figure 12:
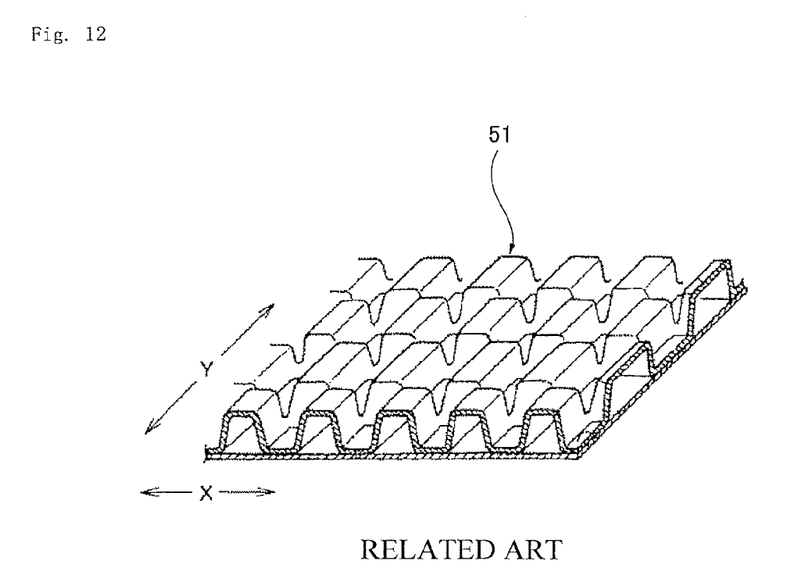
FIG. 12 is a cutaway perspective view of Example 2 of a conventional front surface sheet.

As illustrated in FIG. 12, Japanese Unexamined Patent Application Publication No. 2004-174234 proposes a front surface sheet 51 for an absorbent article used in a skin abutment side of the absorbent article. The proposed sheet comprises a top layer consisting of a sheet-like material which faces the skin side of a wearer and substantively does not expand and a bottom layer consisting of a sheet-like material which is arranged in an absorber side and substantively does not expand, and said top layer and said bottom layer are partially bonded so as to form numerous bonding portions. Said to layer protrudes to the skin side of a wearer in other area except said bonding portion, forming numerous convex portions hollow inside. The convex portion and the bonding portion are arranged alternately forming columns in one direction, and further a plurality of said columns are arranged such that with respect to any one of convex portions in one column, in the right and left columns adjacent to said column, the convex portion is not adjacent to the convex portion.

The front surface sheet of the absorbent article of Japanese Unexamined Patent Application Publication No. 2002-165830 presented a problem in that since the convex portions and concave portions (bonding portions) were continuing in one direction linearly in parallel and the convex portion was continuing in one direction, an air passage which significantly reduced the dampness was created, however, since the concave portions (bonding portions) were also continuing in one direction, a body fluid easily leaked down along the concave portions as flow channels.

In contrast, in the case of the front surface sheet of the absorbent article of Japanese Unexamined Patent Application Publication No. 2004-74234, it presented a problem in that since the convex portions and the concave portions were arranged in a zigzag pattern and had excellent absorbency to prevent a body fluid from leaking down, however, the air did not easily pass through, creating dampness.

The main object of this invention is to provide an absorbent article to reduce dampness and prevent a body fluid from leaking down, provided with a front surface sheet soft to skin having a decreased area in contact with the skin and the manufacturing method therefor.

As the invention of a first aspect of the invention, in order to solve the problem, an absorbent article with an absorber disposed between a permeable front surface sheet and a rear surface sheet of a non-woven fabric is provided, in which the front surface sheet is provided with convex portions in a ridge shape continuing in a longitudinal direction of the absorbent article at a specified interval in the width direction of the absorbent article and provided with dot like concave embossments at a right side adjacent position and a left side adjacent position alternately at an interval in the longitudinal direction of the absorbent article on the both sides of each convex portion, and the concave embossments are arranged in a zigzag pattern as a whole.

According to the aforementioned first aspect of the invention, the front surface sheet is provided with a ridged convex portion continuing in the longitudinal direction of the absorbent article at a specified interval in the width direction of the absorbent article. The concave embossments (bonding portion) securing the front surface sheet is provided with dot-like concave embossments at the right side adjacent position and the left side adjacent position alternately at an interval in the longitudinal direction of the absorbent article on the both sides of each convex portion. The concave embossments are arranged in a zigzag pattern as a whole.

Therefore, the convex portion continuing in the longitudinal direction creates an air passage to reduce dampness. Since the concave embossments securing the front surface sheet are arranged in a zigzag pattern in dots at the right side adjacent position and the left site adjacent position alternately at an interval in the longitudinal direction of the absorbent article on the both sides of each convex portion, the passage of the body fluid becomes a zigzag pattern defined by the concave embossments, thereby preventing the body fluid from leaking down.

Furthermore, even if the body fluid passes through the front surface sheet to flow into the convex portion, the passage in this convex portion alternately expands and shrinks the passage width such that the body fluid does not flow easily and yet is easily absorbed in the absorber side, thereby preventing the body fluid from leaking down.

In a second aspect of the invention, in the absorbent article of the first aspect of the invention, in the front surface sheet in a cross section passing the concave embossment in the width direction, an inclined surface to the concave embossment on the side adjacent to the convex portion is relatively steep, an inclined surface to the concave embossment on the side distant to the convex portion is relatively gentle, and the cross sectional shape of the convex portion is asymmetrical.

Thus, the second aspect of the invention is related to the cross sectional shape of the convex portion, in which an inclined surface to the concave embossment on the side adjacent to the convex portion is relatively steep, an inclined surface to the concave embossment on the side distant to the convex portion is relatively gentle, and the cross sectional shape of the convex portion is asymmetrical with the top as the border.

Therefore, it is possible to reduce the skin contact area, and when a body pressure is received from the front surface side, the cross-sectional shape of the convex portion forms an asymmetrical form bordering the top, and the both walls of the convex portion has a smaller resistance force than the resisting asymmetrical shape to the pressure which is easier to collapse, hence the area becomes softer to the skin.

As a third aspect of the invention, in the absorbent article of the second aspect of the invention, the height of the convex portion is 1-3 mm and the height at the center point position of the inclined surface having a gentle gradient is 0.5-2 mm.

The third aspect of the invention defines the height dimension of the convex portion of the front surface sheet. Specifically, it is desirable that the height at the top of the convex portion be 1-3 mm and the height at the center point position (a half point of a distance between the top and the concave embossments) of the inclined surface having a gentle gradient be 0.5-2 mm.

As a fourth aspect of the invention, in the absorbent article of any of the first to third aspects of the invention, in which regarding the concave embossments, it is desireable that their dimension in the longitudinal direction of the absorbent article is 0.3-4 mm, their dimension in the width direction of the absorbent article is 0.3-3 mm, and their center-to-center interval in the longitudinal and the width directions of the absorbent article is 2-15 mm.

As a fifth aspect of the invention, the manufacturing method of the absorbent article described in any of the first to fourth aspects of the invention is provided, wherein:
the front surface sheet is inserted between a pair of first concave convex roll and second concave convex roll facing each other so as to form the convey portion and concave embossments;
regarding the first concave convex roll, a convex strip portion continuing in the line direction is formed at an interval in the line width direction, the convex strip portion is a wavy convex strip portion with a left convex curved portion protruding to the left side and a right convex curved portion protruding to the right side alternately repeated in a planar view, and the inner surface side of the left convex curved portion and the inner surface side of the right convex curved portion are an arc-shaped curved portion;
the second concave convex roll has a dot-like convex portion at a position corresponding to the arc-shaped curved portion on the inner surface side of the left convex curved portion of the first concave convex roll, and a dot-like convex portion at a position corresponding to the arc-shaped curved portion on the inner surface side of the right convex curved portion, and these dot-like convex portions are arranged in a zigzag pattern;
after the front surface sheet is inserted between the first concave convex roll and the second concave convex roll, it is removed from the first concave convex roll to rotate while it is maintained on the second concave convex roll side. Thereafter, it is introduced between the second concave convex roll and the flat roll provided facing each other, and a second sheet non-woven fabric is introduced between the second concave convex roll and the flat roll such that the front surface sheet and the second sheet non-woven fabric are bonded at a position corresponding to the dot-like convex portion of the second concave convex roll; and
in the subsequent assembly process, an absorber is placed on the top sheet of the rear surface sheet and on the top thereof a front surface sheet in which the second sheet non-woven fabric is laminated on the entirety of the bottom surface side is placed.

The fifth aspect of the invention relates to the manufacturing method of this absorbent article, defining the manufacturing method of a particularly suitable front surface sheet.

Specifically, it is a common method in that the convex portion and the concave embossments are provided in the process of inserting between a pair of first concave convex roll and second concave convex roll facing each other, however, according to this manufacturing method the first concave convex roll, a convex strip portion continuing in the line direction is formed at an interval in the line direction, the convex strip portion is a wavy convex strip portion with a left convex curved portion protruding to the left side and a right convex curved portion protruding to the right side alternately repeated in a planar view, and the inner surface side of the left convex curved portion and the inner surface side of the right convex curved portion are an arc-shaped curved portion.

In contrast, the second concave convex roll has a dot-like convex portion at a position corresponding to the arc-shaped curved portion on the inner surface side of the left convex curved portion of the first concave convex roll, specifically a substantial center point position of the arc-shaped curved portion on the inner surface side and a dot like convex portion at a position corresponding to the arc-shaped curved portion on the inner surface side of the right convex curved portion, specifically at a substantial position of the arc-shaped curved portion on the inner surface side, and these dot-like convex portions are arranged in a zigzag pattern.

The convex strip portion of the first concave convex roll to form the convex portion of the front surface sheet is not to be formed linear but the wavy convex portion in which the left convex curved portion protruding to the left and the right convex curved portion protruding to the right in a planar view are alternately repeated. The inner surface side of the left convex curved portion and the inner surface side of the right convex curved portion are an arc-shaped curved portion, and the dot-like convex portion of the second concave convex roll to form the concave embossments in the front surface sheet is positioned at a substantial center point position of what is surrounded by the arc-shaped curved portion.

Therefore, since the dot-like convex portion of the second concave convex roll is at the substantial center point position of what is surrounded by the arc-shaped curved portion of the first concave convex roll, and the distance from this dot-like convex portion to the arc-shaped curved portion of the first concave convex roll is substantially equal, it is possible to prevent the front surface sheet from being cut off effectively in order to give the concave embossments.

The convex strip portion of the first concave convex roll is the wavy convex strip portion, however, the ridged convex portion formed on the front surface sheet in a product is formed substantially linear due to the restoration force of the non-woven fabric.

As detailed above according to this invention, it is possible to provide an absorbent article to reduce stuffiness and prevent a body fluid from leaking down, provided with a front surface sheet soft to skin having a decreased area in contact with the skin.

Furthermore, according to the manufacturing method of this invention, in order to emboss the front surface sheet, it is possible to give concave embossments at a position adjacent to the convex portion while preventing the sheet from being cut off.

BRIEF DESCRIPTION OF THE DRAWINGS

FIG. 4 are (A) A cross section view along 4A-4A of FIG. 3, (B) a cross section view along 4B-4B of FIG. 3 illustrating a cross section view of a front surface sheet 3.

FIG. 6 are (A) An exploded view of an occlusal surface, (B) a cross section view thereof illustrating an engagement portion (VI portion of FIG. 5) of a first concave convex roll 10 and a second concave convex roll 11.

FIG. 7 are (A) A cross section view of a main portion, (B) a planar view thereof illustrating a first concave convex roll 10.

FIG. 8 are (A) A planar view of a main portion, (B) a cross section view of a main portion illustrating a second concave convex roll 11.

DETAILED DESCRIPTION OF THE INVENTION

The embodiments of this invention will be detailed below by referencing the drawings.

[Structure Example of an Absorbent Article (Incontinence Liner) 1]

Figure 1:
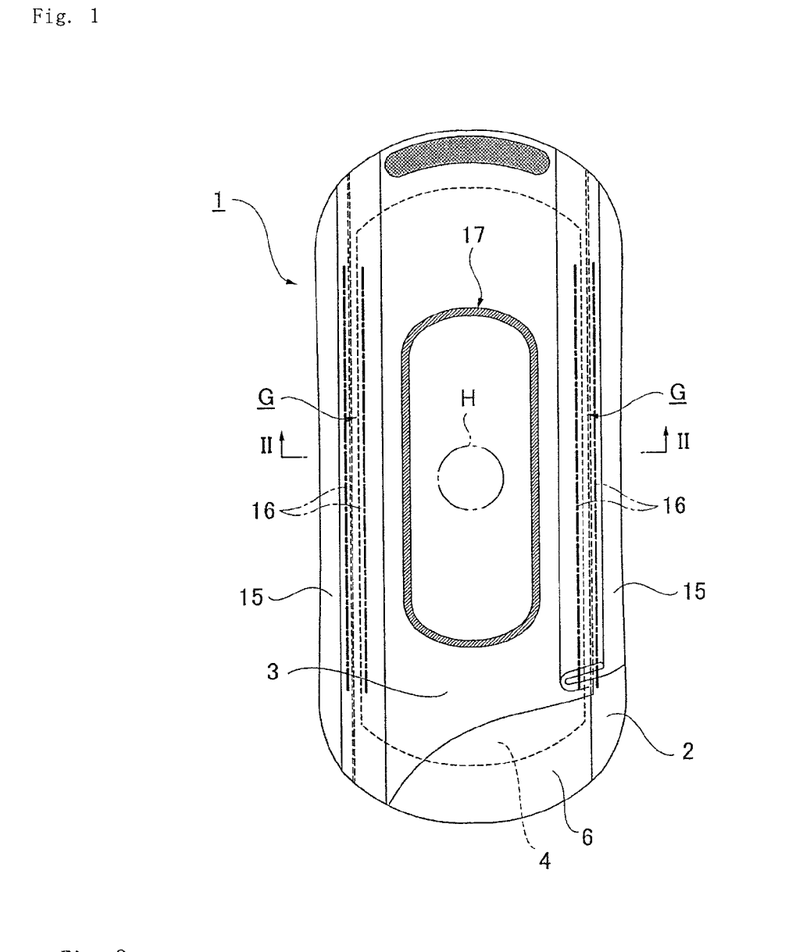
FIG. 1 is a partially cutaway perspective view of an absorbent article (incontinence liner) 1 of this invention.

The Incontinence liner 1, as illustrated in FIG. 1, has a structure comprising an absorber 4 or an absorber 4 enclosed with a crepe paper 5 as illustrated in FIG. 1 disposed between a non-permeable rear surface sheet 2 and a permeable front surface sheet 3 (hereafter referred to as a front surface sheet), a hydrophilic second sheet (non-woven fabric) 6 which is arranged between the front surface sheet 3 and the absorber 4, and standing gathers G, G in the both sides of the front surface side. The non-permeable rear surface sheet 2 includes at least a sheet material having water shielding properties such as polyethylene, polypropylene, or the like. In addition, a non-woven fabric sheet (in this case, a waterproof film and a non-woven fabric constitute a non-permeable rear surface sheet) can be used in which a waterproof film is disposed to ensure substantively non-permeable properties. In recent years, those having moisture permeability tend to be preferably used from the viewpoint of preventing dampness. As a water shielding and permeable sheet material, a micro-porous sheet is preferably used which is obtained by forming a sheet by melt-kneading an inorganic filler into polyethylene, polypropylene, or the like, film of which is to be drawn uniaxially or biaxially.

The front surface sheet 3 comprises a skin abutment surface layer and in this invention a non-woven fabric is used. This front surface sheet 3 forms convex and concave shapes with convex portions 7, 7 in a ridge shape continuing in a longitudinal direction of the liner 1 and concave embossments 8a, 8b provided by a zigzag pattern. Fit embossments 17 in a small oval shape are formed surrounding a urination site H in the top surface of the front surface sheet 3. This front surface sheet 3 will be detailed more specifically below.

The absorber 4 disposed between the non-permeable rear surface sheet 2 and the front surface sheet 3 includes those in which superabsorbent resin is mixed in pulp or chemical fibers and superabsorbent resin are mixed in pulp for use. As illustrated in the drawing, it is desirable that the absorber 4 be enclosed with a crepe paper 5 to maintain the shape, to quickly disperse menstrual bleeding or the like, and to prevent the menstrual bleeding absorbed from flowing back. The pulp includes chemical pulp obtained from wood, cellulose fibers such as melting pulp or the like, or those consisting of artificial cellulose fibers such as rayon, acetate, or the like. Softwood pulp having long fibers is more preferably used than hardwood pulp in terms of the features and prices.

Synthetic fibers may be also mixed in the absorber 4. For example, the synthetic fiber can include polyolefin such as polyethylene, polypropylene, or the like; polyester such as polyethylene terephthalate, polybutylene terephthalate, or the like; polyamide such as nylon or the like; and copolymers thereof for use. Two kinds thereof may be mixed. It is also acceptable to use composite fibers such as core-sheath type fibers with the core thereof having a high melting point and the sheath of a low melting point, side-by-side type fibers, split type fibers, or the like. When the synthetic fiber is a hydrophobic fiber such that it has a high affinity for a body fluid, it is desirable to use fibers surface-treated by a hydrophilic agent.

The suberabsorbent resin includes, for example, resins having a water-swellable polymer partially cross-linked such as polyacrylate cross-linked products, self-crosslinked polyacrylic acid salts, saponified products of acrylic acid ester-vinyl acetate copolymer cross-linked products, isobutylene-maleic anhydride copolymer cross-linked products, polysulfone salts cross-linked products, polyethylene oxide, polyacrylamide, or the like. Acrylic acid or acrylic acid salts excellent in water absorption and water absorption rate is suitable among them. By adjusting the cross-link density and cross-link density gradient, it is possible to adjust the water absorption power and water absorption speed in the manufacturing process of a superabsorbent resin having the water absorption performance. It is desirable that the content rate of the superabsorbent resin be 10-60% of the absorption weight. When the superabsorbent resin content ratio is below 10%, it cannot give a sufficient absorption capacity. When the content ratio exceeds 60%, it does not have any entanglement among the pulp fibers, decreasing the sheet strength so as to easily tear off or crack.

It is acceptable that the hydrophilic second sheet 6 arranged between the permeable front surface sheet 3 and the absorber 4 be hydrophilic to the body fluid. Specifically, it is possible to use materials which are originally hydrophilic by using regenerated fibers such as rayon, cupra, or the like or natural fibers such as cotton or the like; or use fibers which are made hydrophilic by using a hydrophilic agent to surface-treat synthetic fibers such as olefin including polyethylene, polypropylene, or the like, or polyester, polyamide, or the like. It is acceptable that the second sheet 6 have a porous film layer on the rear surface sheet side (absorber 4 side) to give stiffness, or be a laminated layer sheet of a crepe paper, or that furthermore a material including pulp be used.

This incontinence liner 1 has side non-woven fabrics 15, 15 provided on the both sides of the front surface sheet along the longitudinal direction over the entire length of the incontinence liner 1. The outer side portion of these side non-woven fabrics 15, 15 is extended to the side and the non-permeable rear surface sheet 2 is extended to the side. These side non-woven fabric 15 portion and non-permeable rear surface sheet 2 portion extended to the side are bonded with hot-melt adhesives or the like to form a side portion flap.

As the side non-woven fabric 15, from the point of important functions, it is possible to use a water-repellent or hydrophilic non-woven fabrics. For example, when functions such as preventing urine, discharges, or the like from seeping in or increasing favorable skin touch are emphasized, it is desirable to use water-repellent non-woven fabrics coated with silicon-based, paraffin-based, or alkyl chromic chloride-based water repellent, or the like. When the absorption of body fluids is emphasized, it is desirable to use a method in the manufacturing process of synthetic fiber, for example, to allow a compound having a hydrophilic group to coexist for polymerization such as oxidation products of polyethylene glycol or the like, or a method to treat a compound with a metal salt such as stannic chloride or the like to make the surface thereof partially dissolve to be porous so as to deposit metal hydroxides, or the like such that hydrophilic non-woven fabrics can be used in which synthetic fibers are made swollen or porous to make them hydrophilic by means of a capillary phenomenon. As such a side non-woven fabric 15, it is possible to use natural fibers, synthetic fibers, regenerated fibers, or the like as a material formed by an appropriate processing method, however, it is desirable to use non-woven fabrics having air permeability by suppressing the basis weight.

Figure 2:
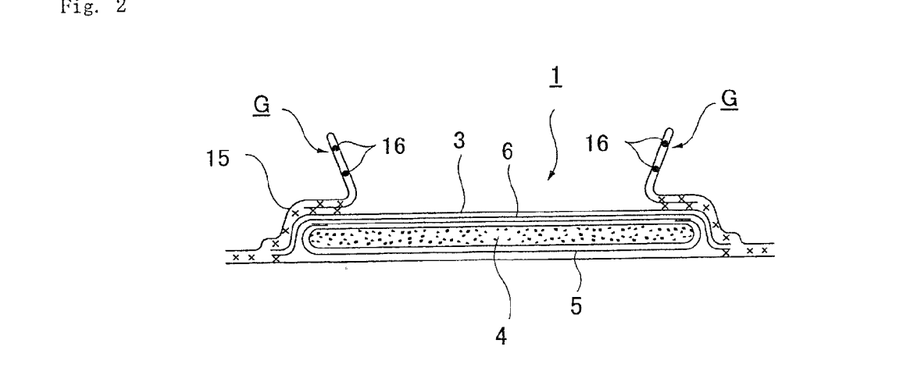
FIG. 2 is a cross section view (II-II arrow view in FIG. 1) of an absorbent article (incontinence liner) 1.

In the inner side of the side non-woven fabric 15, as illustrated in FIG. 2, the side non-woven fabric 15 is substantially folded back, and inside this dual sheet, at the center of the height direction thereof, one or a plurality of filamentous resilient expanding members 16, 16 (two in the illustrated example) are arranged with the both ends or an appropriate position of the longitudinal direction being secured such that the contractile force thereof is used to make the dual sheet portion stand to the surface side forming standing gathers G, G.

[Structure of Front Surface Sheet 3]

The front surface sheet 3 comprises a non-woven fabric. A material fabric constituting this non-woven fabric includes; for example, synthetic fibers such as olefin including polyethylene, polypropylene, or the like, polyester, polyamide, or the like; regenerated fibers such as rayon, cupra, or the like; natural fibers such as cotton or the like. Non-woven fabrics obtained by an appropriate processing method such as an air-through method, spunlace method, spunbond method, thermal bonding method, melt-blown method, needle punch method, or the like can be used. Among these processing methods, the spunlace method is excellent in the flexibility; the spunbond method is excellent in the drape property; and the air-through method and thermal bond method are excellent in the bulkiness and softness. The fibers of non-woven fabrics can be either long or short, however, it is preferred to use short fibers so as to give a towel texture. It is recommended to use olefin fibers such as polyethylene, polypropylene, or the like having a relatively low melting point so as to facilitate the embossing process. It is also suitable to use composite fibers such as core-sheath type fibers with the core thereof having a high melting point, side-by-side type fibers, split type fibers, or the like.

Figure 3:
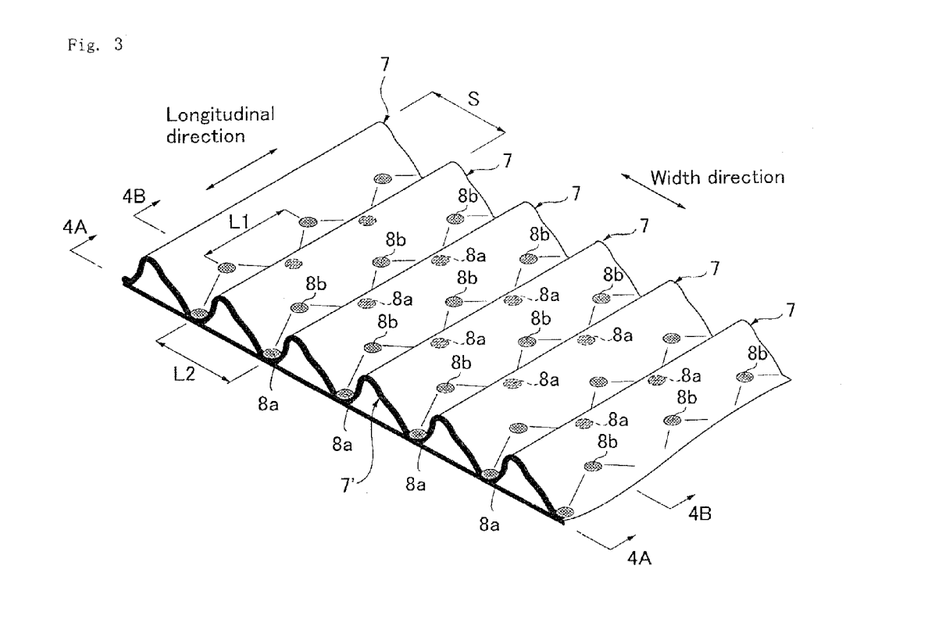
FIG. 3 is an enlarged perspective view of a front surface sheet 3 of this invention.

As illustrated in FIG. 3, the front surface sheet 3 has ridged convex portions 7, 7, continuing in the longitudinal direction of the liner 1 in the width direction of the incontinence liner 1 at specified interval S. It also has dot-like concave embossments 8a, 8b alternately provided at a right side adjacent position and a left side adjacent position on the both sides of each of the convex portions 7, 7 in the longitudinal direction of liner 1 at an interval. The concave embossments 8a, 8b are arranged in a zigzag pattern in a rough positive grid as a whole. That is to say, when the convex portion 7 given with sign 7' in FIG. 3 is viewed, the concave embossment 8b at the right side adjacent position in the longitudinal direction at an interval and the concave embossment 8a at the left side adjacent position are alternately given and these concave embossments 8a, 8b are arranged in a zigzag pattern in a rough positive grid.

Figure 4A:
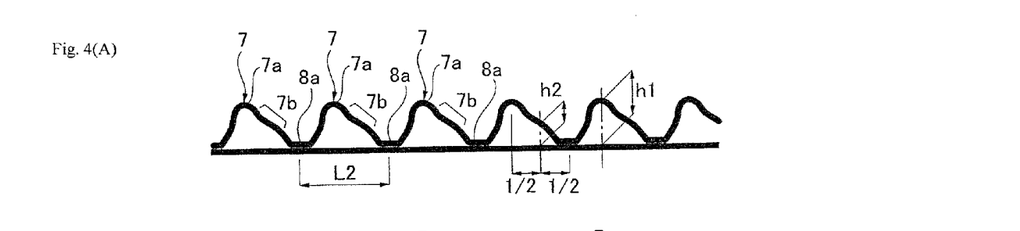

Regarding the cross-sectional shape of the convex portion 7, in the cross section along 4A-4A of FIG. 3, as illustrated in FIG. 4(A), the concave embossments 8a, 8b are arranged in a zigzag pattern in a rough positive grid. As a result thereof, one of the concave embossments 8a (8b) adjacent to the convex portion 7 in the cross-sectional direction is at a relatively adjacent position, while the other is at a relatively distant position. Because of this, the inclination of the inclined surface of the concave embossment 8a on the adjacent side to the convex portion 7 is relatively steep, the inclination of the inclined surface of the concave embossment 8a to the convex portion 7 on the distant side is relatively gentle, and the cross-sectional shape of the convex portion 7 forms an asymmetrical shape. Herein, in this specification, the top of the convex portion 7 is defined to be a high convex portion 7a and the center point of the inclined surface having a gentle gradient is defined to be a low convex portion 7b.

Figure 4B:
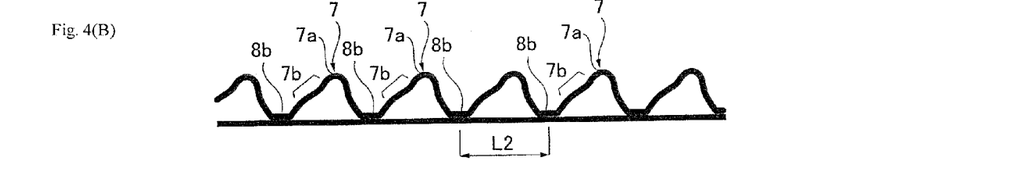

In the cross section along 4B-4B of FIG. 3, since the relationship of the concave embossment 8b adjacent to the convex portion 7 and the concave embossment 8b at a distant position is opposite, as illustrated in FIG. 4(B), an inclined surface having a steep gradient is formed on the right side of the convex portion 7, while an inclined surface having a gentle gradient is formed on the left side.

It is desirable that the height h1 of the high convex portion 7a be 1-3 mm, and the height h2 of the position of the low convex portion 7b (for convenience, a half point between the high convex portion 7a and the concave embossment 8a) be 0.5-2 mm. It is also desirable that the concave embossment 8a (8b) be in a circular or oval shape with the longitudinal directional dimension of the liner 1 being 0.3-4 mm and the width directional dimension of the liner 1 being 0.3-3 mm, and the longitudinal directional interval L1 and the width directional interval L2 (distance on the same column line) of the liner 1 be 2-15 mm.

Next, the convex portions 7, 7 and the concave embossments 8a, 8b given on the front surface sheet 3 will be detailed based on FIG. 5-FIG. 10 in terms of the manufacturing method of embossing these.

Figure 5:
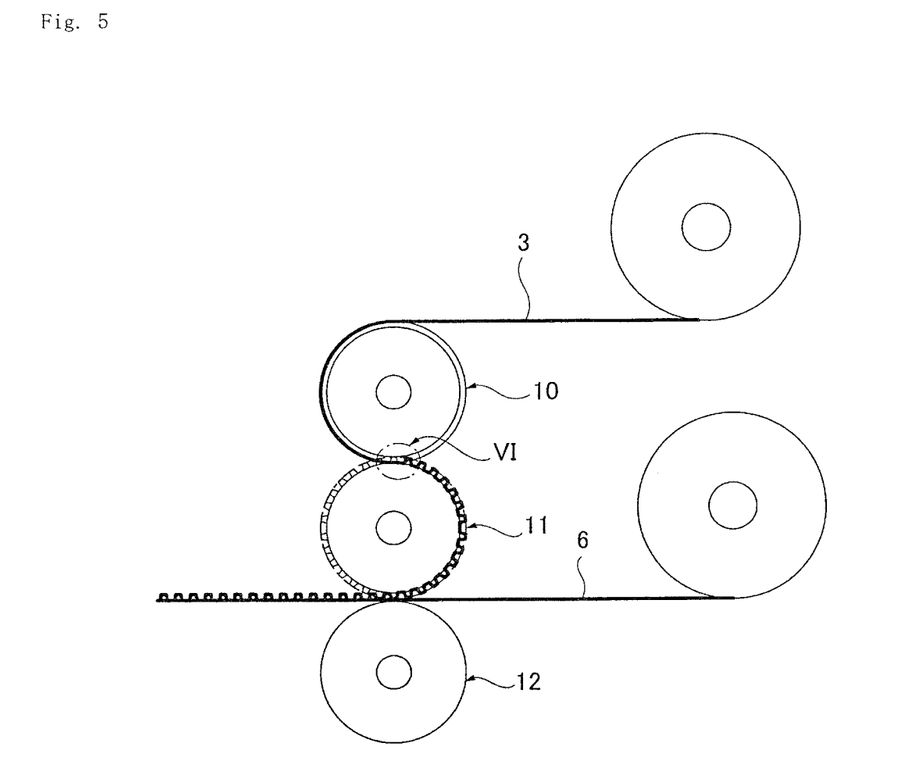
FIG. 5 is a schematic diagram of a manufacturing method of a front surface sheet 3.

As illustrated in FIG. 5, the front surface sheet 3 is inserted between a pair of first concave convex roll 10 and second concave convex roll 11 facing each other such that the convex portions 7, 7 and concave embossments 8a, 8b are given, and after it is inserted between the first concave convex roll 10 and the second concave convex roll 11, it is removed from the first concave convex roll 10 to rotate while being held on the second concave convex roll 11 side. Thereafter, it is introduced between the second concave convex roll 11 and the flat roll 12 provided facing each other, a second sheet non-woven fabric 6 is introduced between the second concave convex roll 11 and the flat roll 12, the front surface sheet 3 and the second sheet non-woven fabric 6 are subjected to heated-pressure bonding at a position corresponding to the convex portion of the second concave convex roll 11.

According to the illustrated example, the first concave convex roll 10, the second concave convex roll 11, and a flat roll 12 are vertically arranged in this order from the upper level. After the front surface sheet 3 is supplied on the top side of the first concave convex roll 10 to be rotated a half cycle, it is introduced in an engagement portion of the first concave convex roll 10 and the second concave convex roll 11. Thereafter the second concave convex roll 11 is rotated a half cycle and then it is bonded with the second sheet non-woven fabric in the engagement portion of the second concave convex roll 11 and the flat roll 12.

Figures 6A, 6B:
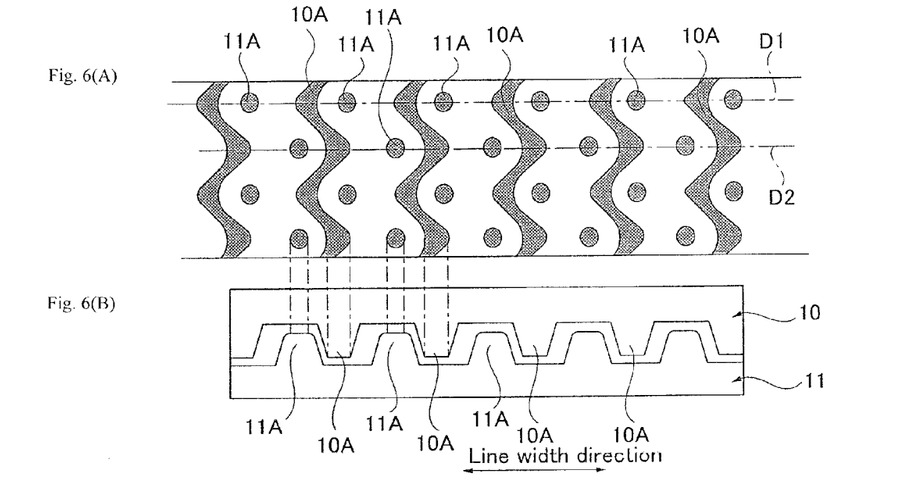

In the engagement portion VI of the first concave convex roll 10 and the second concave convex roll 11, as illustrated in FIG. 6, the convex portions 7, 7 and the concave embossments 8a, 8b are provided on the front surface sheet by engaging the convex strip portions 10A, 10A provided in the first concave convex roll 10 with the dot-like convex portions 11A, 11A provided in the second concave convex roll 11.

Figures 7A, 7B:
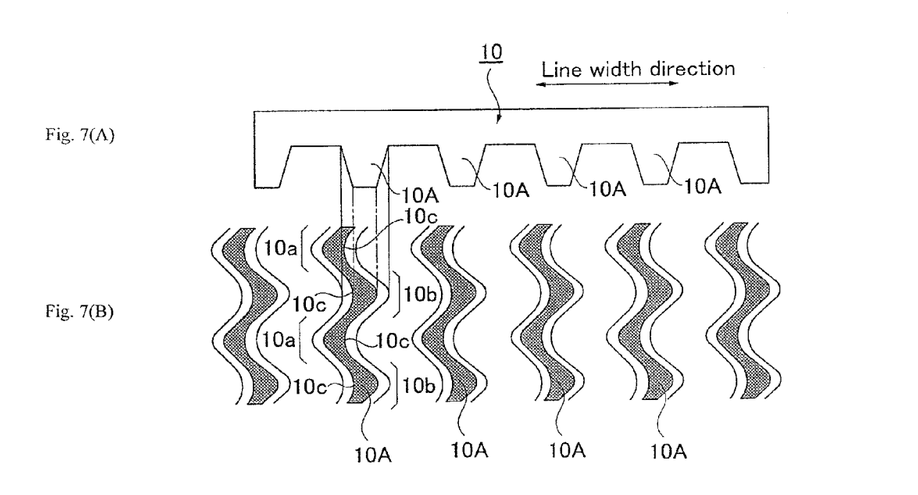

In the first concave convex roll 10, as detailed in FIG. 7, the convex strip portion 10A continuing in the line direction is formed in the line direction at an interval, the convex strip portion 10A is a wavy convex strip portion with a left convex curved portion protruding to the left side 10a and a right convex curved portion protruding to the right side 10b alternately repeated in a planar view, and the inner surface side of the left convex curved portion 10a and the inner surface side of the right convex curved portion 10b are an arc-shaped curved portion.

Figures 8A, 8B:
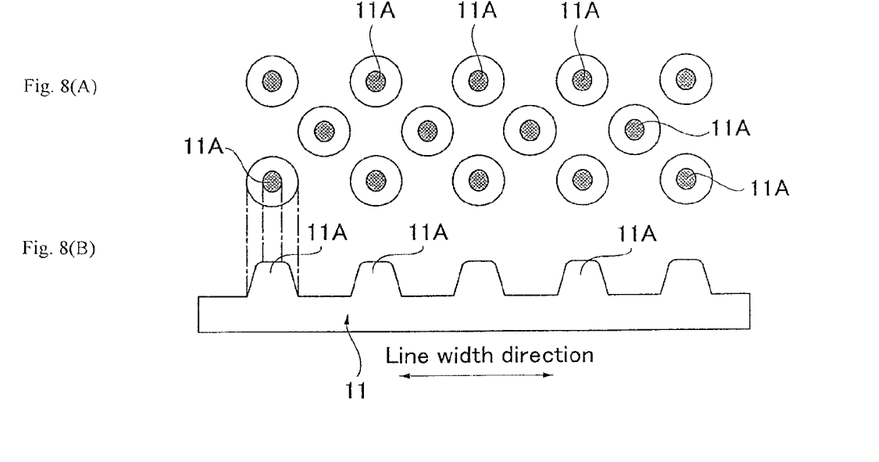

In contrast, as detailed in FIG. 8, the second concave convex roll 11 has the dot-like convex portion 11A at a position corresponding to the arc-shaped curved portion on the inner surface side 10c of the left convex curved portion 10a of the first concave convex roll 10, i.e., a position corresponding to a substantial center point of the arc-shaped curved portion on the inner surface side 10c. And it also has the dot-like convex portion 11A at a position corresponding to the right convex curved portion 10b of the arc-shaped curved portion on the inner surface side 10c, i.e., a substantial center point of the arc-shaped curved portion on the inner surface side 10c, and these dot-like convex portions 11A, 11A are arranged in a zigzag pattern of positive grids as a whole. The engagement of the first concave convex roll 10 and the second concave convex roll 11 is as illustrated in FIG. 6(A).

As it is clearly understood from FIG. 6(A), on the transversal line D1 passing through the left convex curved portion 10a, the dot-like convex portion 11A positioned on the right is at an adjacent position, while the dot like convex portion 11A positioned on the left is at a distant position. Furthermore, on the transversal line D2 passing through the right convex curved portion 10b, the dot-like convex portion 11A positioned on the right is at a distant position, while the dot-like convex portion 11A positioned on the left is at an adjacent position.

Figure 9:
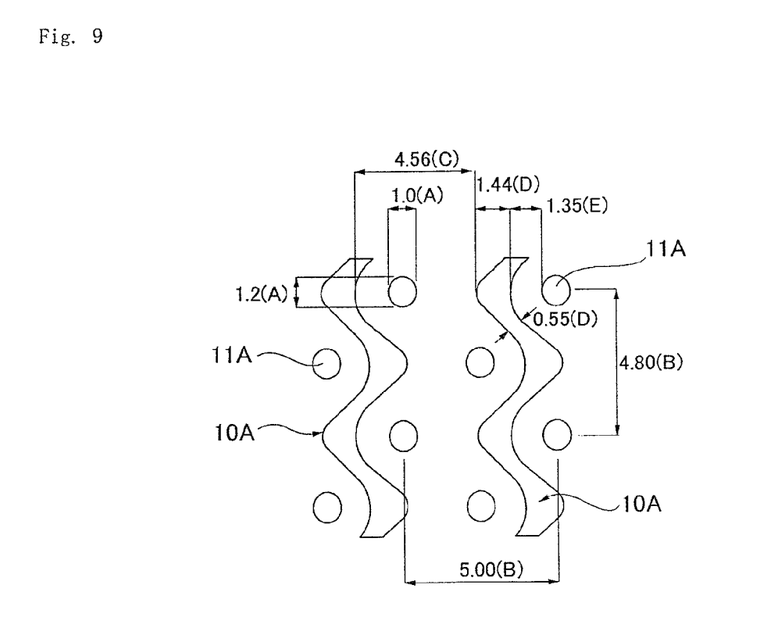
FIG. 9 is a diagram illustrating dimension examples of a convex strip portion of a first concave convex roll 10 and a dot-like convex portion of a second concave convex roll 11.

A dimension example of the convex strip portion 10A of the first concave convex roll 10 and the dot-like convex portion 11A of the second concave convex roll 11 will be illustrated in FIG. 9.

The tip diameter of the dot-like convex portion 11A of the second concave convex roll 11 may be circular, however, it is desirable that it be an oval shape with the line direction (MD) being slightly longer than the line width direction (CD). In the subsequent process to give fit embossments from the front surface sheet 3 to the absorber 4 side, a problem occurs in that the front surface sheet 3 is pushed into the absorber 4 such that the front surface sheet 3 is pulled to extend to the width direction, easily peeling off the dots. The oval shape long in the line direction, however, has higher bonding strength in the width direction, hardly peeling off the dots. Regarding specific dimensions, it is recommended that the line directional dimension (A) be 0.3-4 mm, preferably 0.8-2.0 mm, while the line width directional dimension (A) be 0.3-3 mm, preferably 0.8-1.5 mm. In the example illustrated, the line directional dimension (A) is 1.2 mm, while the line width directional dimension (A) is 1.0 mm.

It is desirable that the line directional interval (B) and the line orthogonal interval (B) of the dot-like convex portion 11A be 2-15 mm, preferably 3-10 mm. In the example illustrated, the line directional interval (B) is 4.8 mm, while the line orthogonal interval (B) is 5.0 mm.

Regarding the dimension of the convex strip portion 10A of the first concave convex roll 10, it is desirable that the width (D) of the left convex curved portion 10a and the right convex curved portion 10b be 1-2 mm. In the example illustrated, it is 1.44 mm. It is desirable that the width dimension (D) of the bordering portion of the left convex curved portion 10a and the right convex curved portion 10b be 0.5 mm or more. In the example illustrated, it is 0.55 mm. It is desirable that the distance (C) from the tip of the left convex curved portion 10a to the arc-shaped curved portion on the inner surface side 10c of the convex portion 10A adjacent in the width direction be 1-15 mm, preferably 3-10 mm and three times or more than the tip diameter of the dot-like convex portion 11A. In the example illustrated, it is 4.56 mm.

In the engagement portion V of the first concave convex roll 10 and the second concave convex roll 11, the front surface sheet 3 is given with the convex portions 7, 7 and the concave embossments 8a, 8b. This will be further detailed based on FIG. 10 and the effects of the front surface sheet 3 of this invention will be further detailed below.

Figure 10:
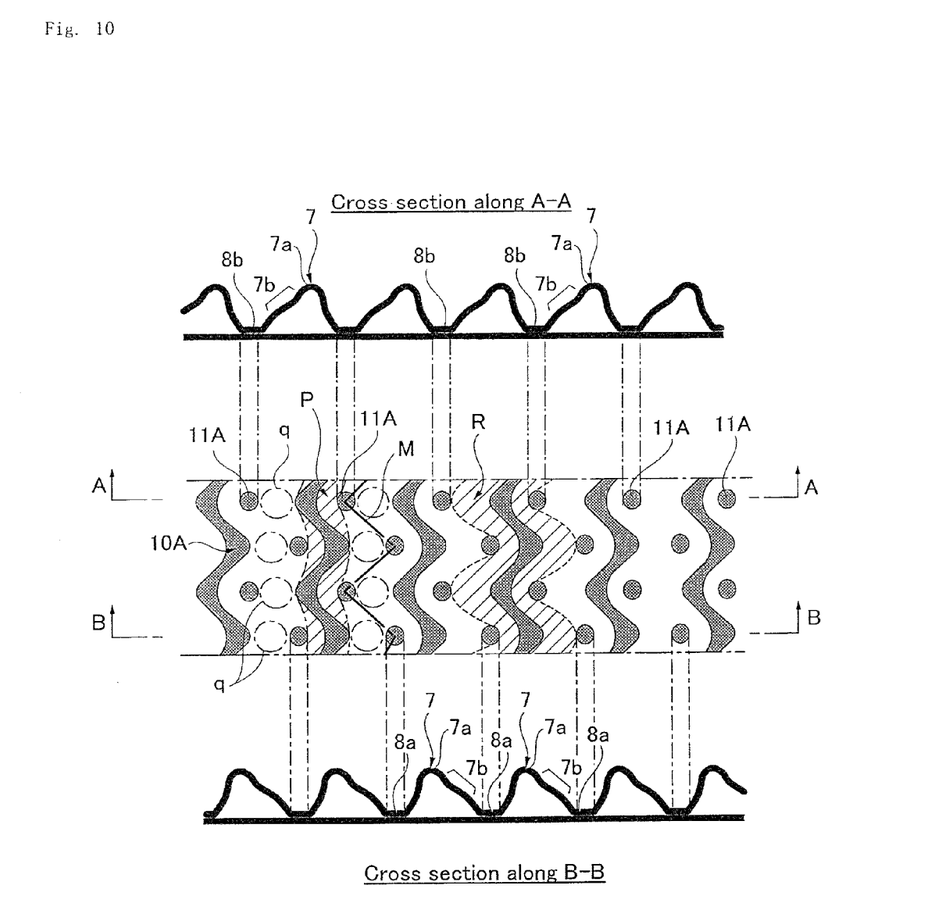
FIG. 10 is a diagram illustrating an embossment state of a first concave convex roll 10 and a second concave convex roll 11 and the effects of a front surface sheet 3.

As described above, the ridged convex portion 7 is formed in the front surface sheet 3 by the wavy convex strip portion 10A formed in the first concave convex roll 10. The convex strip portion 10A is wavy and the convex strip area when given with embossments is the region conceptually shown by the shaded area P. This convex strip area P is also slightly wavy. The front surface sheet 3 consists of a non-woven fabric, and the ridged convex portions 7, 7 are formed substantially linear in a product state by the restoration force thereof. These convex portions 7, 7 form an air passage continuing in the longitudinal direction, reducing the stuffiness.

On a line crossing the convex curved portions 10a, 10b of the convex strip portion 10A, the adjacent dot-like convex portion 11A on one side is at a relatively adjacent position, while the adjacent dot-like convex portion 11A on other side is at a relatively distant position. A spatial region q exists between these dot-like convex portions 11A at a distant position, which forms a low convex portion 7b in the front surface sheet 3 corresponding to this spatial region q. In the front surface sheet 3, the high convex portion 7a and the low convex portion 7b alternately exist in the transverse direction.

Regarding the cross-sectional shape of the convex portion 7 formed in the front surface sheet 3, the inclined surface between the concave embossments 8a (8b) adjacent to the convex portion 7 is an inclined surface having a relatively steep gradient. The inclined surface between the concave embossments 8a (8b) distant from the convex portion 7 is an inclined surface having a relatively gentle gradient. Since the cross-sectional shape of the convex portion 7 forms an asymmetrical shape bordering the top, it is possible to reduce the skin contact area, and when a body pressure is received from the front surface side, the cross-sectional shape of the convex portion 7 forms an asymmetrical form bordering the top, the both walls of the convex portion have a smaller resistance force than the resisting asymmetrical shape to the pressure which is easier to collapse, hence the area becomes softer to the skin.

In contrast, the dot-like convex portion 11A adjacent to the convex strip portion 10A is positioned substantially at a center point surrounded by the arc-shaped curved portion 10c, and the distance from this dot-like convex portion 11A to the arc-shaped curved portion 11c of the first concave convex roll is substantially equal, hence in order to emboss, it is possible to prevent the front surface sheet 3 from being cut off.

A polygonal line M connecting the dot like convex portions 11A, 11A between the convex portions 10A, 10A is in a zigzag pattern. This polygonal line M is a line to become a flow path of the body fluid, which does not flow linearly, hence it is possible to prevent the body fluid from leaking down. Furthermore, even if the body fluid passes through the front surface sheet 3 to flow into the convex portion 7, the passage in this convex portion 7, as illustrated by the shaded area R in FIG. 10, alternately expands and shrinks the passage width such that the body fluid does not flow easily and is easily absorbed in the absorber side, thereby preventing the body fluid from leaking down.

OTHER EMBODIMENTS (1) According to the above embodiment, the convex strip portion 10A formed in the first concave convex roll 10 is a wavy convex strip portion with the left convex curved portion protruding to the left side 10a and the right convex curved portion protruding to the right side 10b alternately repeated in a planar view, however, it is possible to form this convex strip portion 10A in a straight line in the line direction.

The invention claimed is:

1. An absorbent article comprising an absorber disposed between a permeable front surface sheet and a rear surface sheet, the front surface sheet being comprised of a non-woven fabric, wherein
the front surface sheet is provided, at predetermined intervals in a width direction of the absorbent article, with a ridge-shaped portions of predetermined height relative to a base plane of the front surface sheet, the ridge-shaped portions extending in a longitudinal direction of the absorbent article, and
the front surface sheet is also provided with dot-shaped embossments in recessed portions between pairs of adjacent ridge-shaped portions, the dot-shaped embossments being concave in a direction normal to the base plane of the front surface sheet, the dot-shaped embossments in each of the recessed portions being laterally spaced from a longitudinal centerline of the recessed portion and being proximate to a side of one of the ridge-shaped portions adjacent to the recessed portion, the embossments in each of the recessed portions alternating left and right relative to the centerline so that imaginary lines connecting longitudinally successive embossements in the recessed portions are in a zigzag configuration,
and wherein,
in a cross section passing through any one of the dot-shaped embossments in the width direction of the absorbent article, an inclined surface of the dot-shaped embossment on a side of the dot-shaped embossment adjacent to the ridge-shaped portion is steeper than an inclined surface of the dot-shaped embossment on the side of the dot-shaped embossment distant from the ridge-shaped portion, and a cross sectional shape of the ridge-shaped portion is thereby asymmetrical.

2. The absorbent article according to claim 1, wherein height from the base plane to a top of the ridge-shaped portion is 1-3 mm, and
height from the base plane to a center point position of the inclined surface on the side of the dot-shaped embossment distant from the ridge-shaped portion is 0.5-2 mm.

3. The absorbent article according to claim 1, wherein dimension of each of the dot-shaped embossments in the longitudinal direction of the absorbent article is 0.3-4 mm,
dimension of each of the dot-shaped embossments in the width direction of the absorbent article is 0.3-3 mm, and
center-to-center intervals of the dot-shaped embossments in the longitudinal and the width directions of the absorbent article are 2-15 mm.

4. A method of manufacturing the absorbent article claimed in claim 1, comprising:
inserting the front surface sheet in a lengthwise direction thereof between a pair of rotating first concave convex roll and second concave convex roll facing each other so as to form the convex portion and the concave embossments;
wherein in the first concave convex roll, convex strip portions are formed, the convex strip portions extending in the lengthwise direction of the front surface sheet and being spaced from each other at an interval in the width direction of the front surface sheet, wherein each of the convex strip portions is a wavy convex strip portion with a left convex curved portion protruding to the left side and a right convex curved portion protruding to the right side alternately repeated in a planar view, and the inner surface side of the left convex curved portion and the inner surface side of the right convex curved portion are an arc-shaped curved portion;
wherein the second concave convex roll has dot-shaped convex portions at positions corresponding to the arc-shaped curved portion on the inner surface side of the left convex curved portion of the first concave convex roll, and dot-shaped convex portions at a position corresponding to the arc-shaped curved portion on the inner surface side of the right convex curved portion, the dot-shaped convex portions being arranged in a zigzag pattern;
then removing the front surface sheet from the rotating first concave convex roll while maintaining the front surface on the rotating second concave convex roll, then inserting the front surface sheet between the second concave convex roll and a flat roll facing the second concave convex roll, and inserting a non-woven fabric second sheet between the second concave convex roll and the flat roll so that the front surface sheet and the non-woven fabric second sheet are bonded at a position corresponding to the dot shaped convex portion of the second concave convex roll whereby the non-woven fabric second sheet is laminated integrally on a bottom surface side of the front surface sheet; and
in a subsequent assembly process, placing an absorber between the rear surface sheet and the non-woven fabric second sheet laminated integrally on the bottom surface side of the front surface sheet.

* * * * *